United States Patent [19]

Brown et al.

[11] Patent Number: 6,027,450

[45] Date of Patent: *Feb. 22, 2000

[54] TREATING A TOTALLY OR NEAR TOTALLY OCCLUDED LUMEN

[75] Inventors: Peter S. Brown, Mountain View; Paul G. Yock, Hillsborough, both of Calif.

[73] Assignee: Devices for Vascular Intervention, Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/368,314

[22] Filed: Dec. 30, 1994

[51] Int. Cl.$^7$ ..................................................... A61B 8/00
[52] U.S. Cl. ........................................ 600/459; 600/159
[58] Field of Search .................... 128/662.03, 662.05, 128/662.06, 660.08, 660.09, 751; 606/159; 600/454, 455, 459, 462, 466, 467, 468, 439; 601/2

[56] References Cited

U.S. PATENT DOCUMENTS

| | | | |
|---|---|---|---|
| 5,090,414 | 2/1992 | Takano | 128/662.05 |
| 5,257,628 | 11/1993 | Ishiguro et al. | 128/662.06 |
| 5,335,663 | 8/1994 | Oakley et al. | 128/662.05 |
| 5,373,849 | 12/1994 | Maroney et al. | 128/662.06 |
| 5,383,460 | 1/1995 | Jang et al. | 128/662.06 |

*Primary Examiner*—George Manuel
*Attorney, Agent, or Firm*—Heller Ehrman White & McAuliffe

[57] ABSTRACT

A method and system for recanalizing a totally or near totally occluded body lumen such as an artery which has an elongated catheter shaft with means such as a cutting or ablating element at the distal end of the shaft to remove occluding material and with ultrasonic imaging means preferably located on the shaft proximal to the cutting or ablating element to allow the operator to maintain the radial position of the distal end of the catheter shaft within the body lumen so that no contact is made between the cutting or ablating means and the wall defining the body lumen. The imaging system preferably includes one or more ultrasonic transducers which emit ultrasound in a direction having a substantial radial component, or a substantial axial component or both. Ultrasonic energy reflected from the wall defining the body lumen is received by transducers which generate signals representing the received ultrasonic energy, which in turn are used to form an image of the wall on a video monitor and the radial location of the distal end of the catheter shaft or the means to remove occluding material. The image projected on the video monitor may then be used by the physician to control the position of the distal end of the catheter shaft and/or the means to remove occluding material within the body lumen.

21 Claims, 3 Drawing Sheets

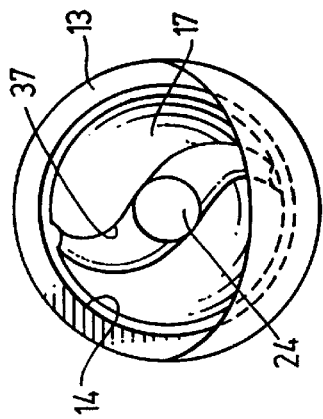
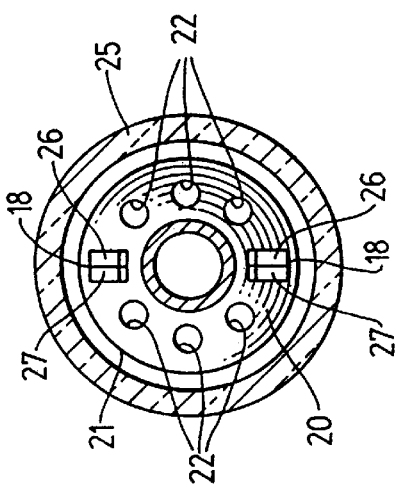
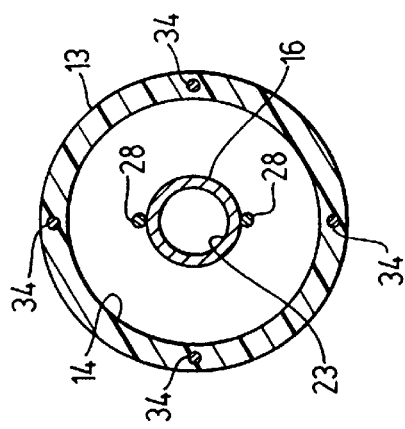
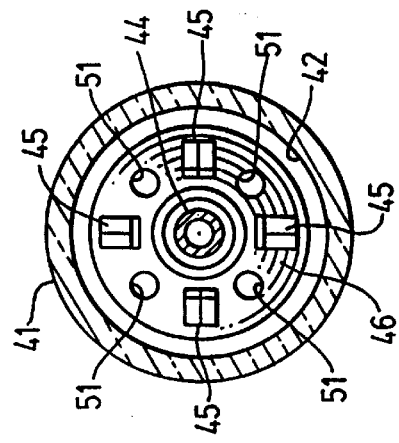
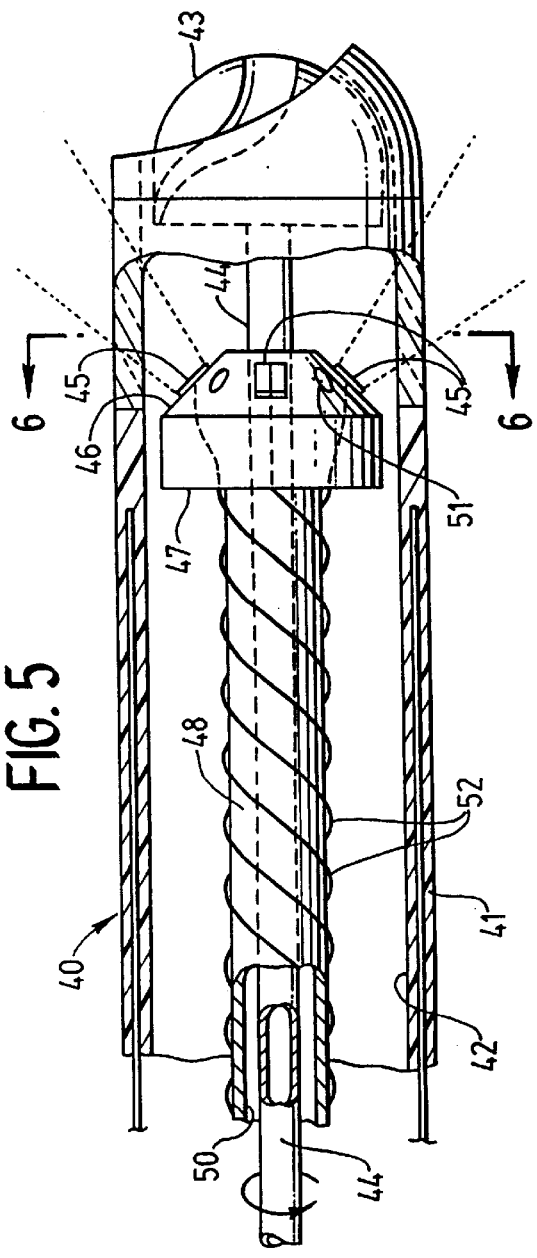

TREATING A TOTALLY OR NEAR TOTALLY OCCLUDED LUMEN

BACKGROUND OF THE INVENTION

This invention generally relates to the treatment of a totally or near totally occluded body lumen and particularly to a catheter for such treatment of blood vessels, e.g. coronary and peripheral arteries.

There are presently several treatment modalities for stenotic or occluded arteries, including balloon and laser angioplasty, atherectomy, by-pass surgery and the like. While each of these treatments has its advantages, each also has its advantages. For example, balloon angioplasty has been found to be highly successful in a wide variety of stenoses, both coronary and peripheral arteries, but there are some stenoses which are too tough to be effectively dilated by an inflatable balloon. Similarly, directional atherectomy has been found to be very successful in soft to medium hardness plaque but is found to be relatively ineffective in very hard, highly calcified plaques.

Laser treatments, hot or cold, and other hot-tipped or heated balloon catheters have also been found to be successful in some stenoses, but the restenosis rate has been disappointingly high. Additionally, the high temperatures frequently developed by some of these devices can damage the arterial lining and can also cause considerable pain.

By-pass surgery has likewise been found to be successful in many instances but such surgery involves a traumatic intrusion into the patient's body and can debilitate the patient for an extended period, even if the treatment is successful.

Ultrasonic ablation of stenotic buildup in peripheral arteries have also been suggested by Don Michael et al. in U.S. Pat. No. 4,870,953. While the ultrasonic treatment has been found to be effective, particularly with highly calcified plaque, the procedure tends to leave a substantial amount of residual blockage.

Total or near total occlusions have presented a particularly difficult problem because most treatment devices which involve intravascular delivery, such as angioplasty, atherectomy and the like, require the treatment device to be advanced into the stenotic region before the treatment can be initiated. Intravascular devices have been introduced having means on their distal ends for removing occluding material to form a channel therein. However, it has been found that very frequently when these devices were advanced through a totally or near totally occluded body lumen the means for removing occluding material on the distal ends of these devices would pass through the wall of the body lumen or otherwise cause damage thereto because the operator would not know where the devices were positioned within the body lumen with respect to the wall defining the body lumen.

What has been needed and has been heretofore unavailable is a treatment system for totally or near totally occluded body lumens, particularly coronary arteries, which can be used to remove or ablate occluding material to recanalize such occluded body lumens with little risk of penetrating or damaging the wall of the body lumen. The present invention satisfies these and other needs.

SUMMARY OF THE INVENTION

This invention is directed to a system and method for the treatment of a totally or near totally occluded region of a patient's body lumen, such as a coronary artery, wherein an image is generated of the wall defining the body lumen to facilitate the safe advancement of an elongated treatment device which has means to remove occluding material on its distal end through the occluded region of the body lumen.

The system of the present invention includes an elongated intraluminal device with means to remove occluding material at the distal end thereof and ultrasonic imaging system on a distal section of the device which emits ultrasonic energy in direction toward the wall of the body lumen. The imaging system also has an ultrasonic energy receiving means which receives ultrasonic energy reflected from the wall of body lumen wall and converts the received ultrasonic energy to one or more signals representing the received energy. An image of the body lumen is formed on a display device such as a CRT or video display device from the signals representing the received ultrasonic energy. The image shown indicates the radial location of the distal end of the device within the body lumen, thereby allowing the operator or physician to guide the distal end of the device through the occluded region of the body lumen while removing occluding material within the lumen without risk of contacting the body lumen wall and causing damage thereto. The ultrasonic energy is directed toward the wall in an axial or radial direction, or preferably in both the axial and radial directions The elongated device of the invention comprises an elongated flexible shaft with at least one inner lumen extending therein, an elongated probe member having proximal and distal ends disposed within the inner lumen, and means on the probe's distal end to remove occluding material. In those instances wherein the means to remove occluding material is a rotating cutting or abrading element, the elongated probe member is rotatably disposed within the inner lumen of the catheter shaft. In those systems in which the ablation means need not be rotated, e.g. means to emit laser, radio frequency or microwave energy, the elongated probe member supporting such ablation means need not be rotated either.

The elongated device has an imaging system preferably located proximal to the means for removing occluding material. The imaging system has means to emit ultrasonic energy at a frequency and amplitude sufficient to cause reflection of emitted ultrasonic energy from the wall defining the body lumen for the real time imaging of the profile of the patient's body lumen. The imaging system is also provided with means for receiving the reflected ultrasonic energy which converts the received energy to signals which are then used to generate a display of the transverse outline of the body lumen. The means for emitting ultrasonic energy and the means for receiving reflected ultrasonic energy may be piezoelectric crystals. The same crystal or separate crystals may be used for the separate functions of emitting and receiving ultrasonic energy. As previously mentioned, the signals representing the reflected ultrasonic energy received by the piezoelectric crystals may then be used to provide the desired image of the body lumen. A plurality of ultrasonic transducers for emission and reception may be disposed in a fixed position in the distal extremity of the catheter shaft, proximal to the means to remove occlusive material. Alternatively, one or more ultrasonic transducers may be mounted for rotation, e.g. on a rotatable shaft, to emit and receive ultrasonic energy. In yet another embodiment, an ultrasonic energy reflector may be mounted for rotation on a rotatable shaft with a ultrasonic transducer fixed adjacent to the rotating reflection. Other ultrasonic imaging systems may be employed.

Preferably, the device is also provided with means, operable from the proximal end of the device which extends out of the patient, for adjusting the radial position of the distal end of the elongated device within the body lumen so as to guide the distal end of the device through the occluded lumen while removing or ablating occluding material with no risk of damage to or penetration through the wall of the body lumen. Suitable means includes control lines secured to the distal end of the device which, when tension is applied thereto, causes the distal tip to deflect. A variety of other means may be used to steer the device through the stenotic region of the body lumen.

By providing a means to move the distal tip of the elongated device within the body lumen and an imaging means which provides real time imaging of the body lumen, the distal end of the device can be guided by the physician while observing the image produced by the imaging system to ensure effective advancement of the means for removing the occluding material through the occluding mass. Moreover, the system allows the physician to observe the amount of residual stenosis which exists after treatment so that further treatments such as conventional angioplasty can be performed.

These and other advantages of the invention will become more apparent from the following detailed description of the invention when taken in conjunction with the accompanying exemplary drawings.

BRIEF DESCRIPTION OF THE DRAWINGS

FIG. 2 is an end elevational view of the device shown in FIG. 1.

FIG. 3 is a transverse cross-sectional view of the device shown in FIG. 1, taken along the lines 3—3.

FIG. 4 is a transverse cross-sectional view of the device shown in FIG. 1, taken along the lines 4—4.

FIG. 5 is an elevational view, partially in section, of an alternative embodiment of the invention.

FIG. 6 is a transverse cross-sectional view of the device shown in FIG. 5, taken along the lines 6—6.

DETAILED DESCRIPTION OF THE INVENTION

Figure 1:
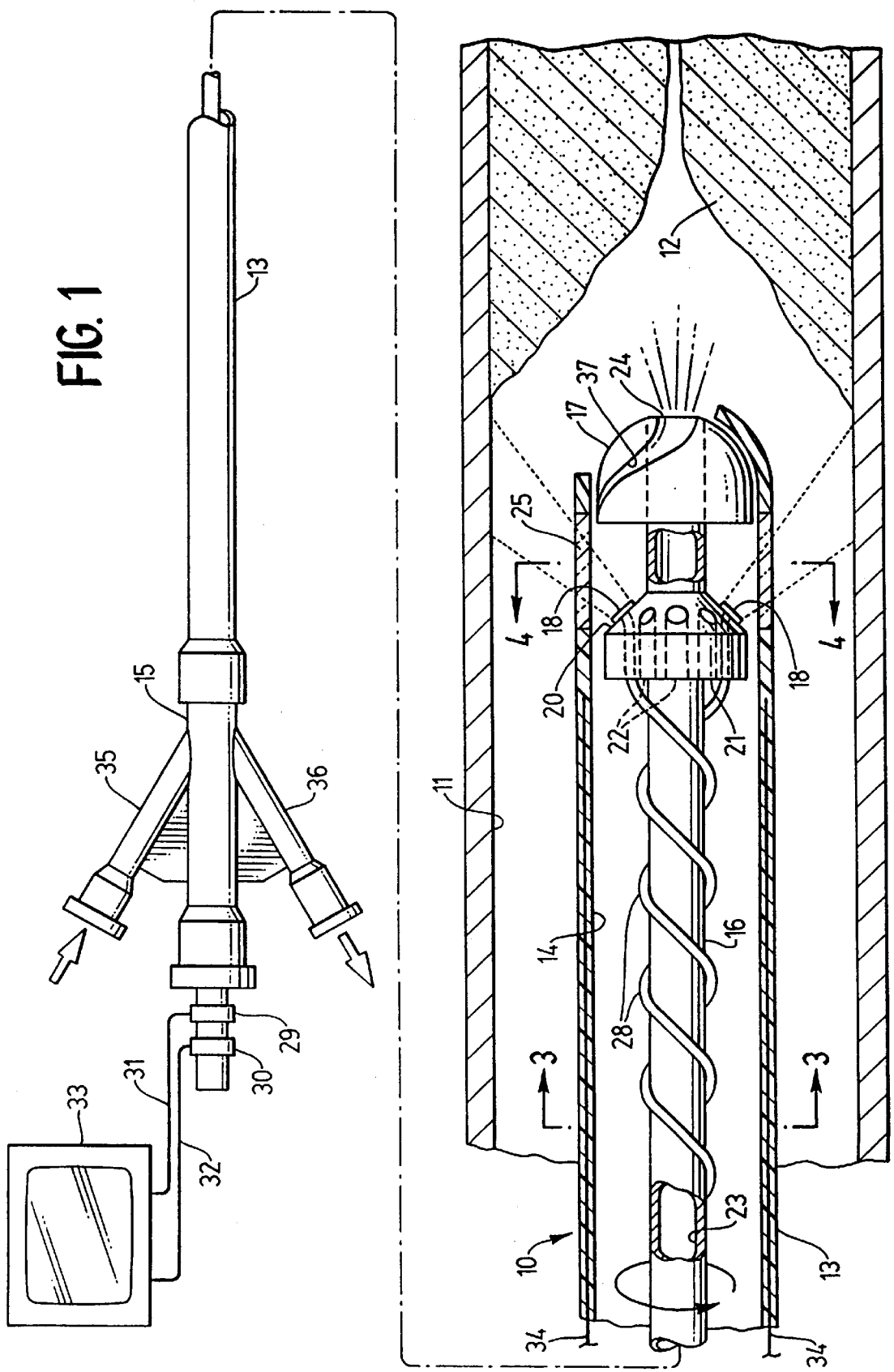
FIG. 1 is an elevational view, partially in section, of an elongated device embodying features of the present invention.

FIGS. 1–4 illustrate a intraluminal catheter 10 embodying features of the invention disposed within a body lumen 11 proximately adjacent to a total or near total occlusion 12 of the body lumen. The catheter 10 has an elongated shaft 13, an inner lumen 14 extending with the shaft, a multiarm adapter 15 on the proximal end of the catheter shaft, a rotatable shaft 16 disposed within the inner lumen 14 having a cutting head 17 on the distal end thereof and at least one piezoelectric element or transducer 18 for emitting and receiving ultrasonic energy mounted on the inclined shoulder 20 of the supporting member 21 on the rotatable shaft 16. As shown more clearly in FIG. 4, the supporting member 21 has a plurality of passageways 22 which allow for the aspiration of occluding material which is severed from the occluded body lumen by the cutting head 17. The rotatable shaft 16 is provided with an inner lumen 23 which may be used to provide fluid through the distal port 24 in the distal end of the catheter 10 and to provide a lumen for the passage of a guidewire.

The shaft 13 is provided with a distal wall portions 25 which are made of material which readily transmits ultrasonic energy, i.e. act as windows, as depicted schematically in FIG. 1. The supporting member 21 may be an integral part of the shaft 16 so that rotation of the shaft to rotate the cutting head 17 also rotates the piezoelectric transducers 18 mounted on the inclined shoulders 20.

Figure 7:
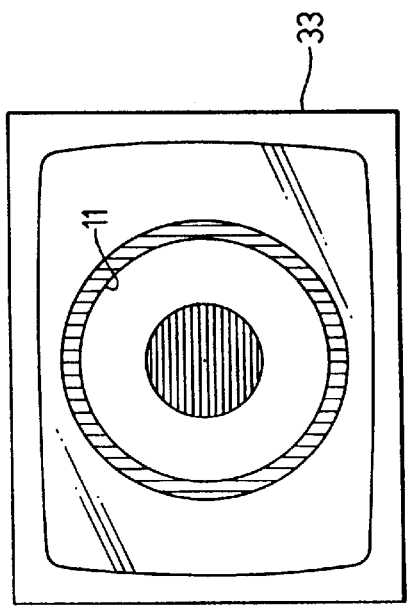
FIG. 7 is schematic representation of a video monitor displaying an idealized image of the transverse outline of a body lumen.

The ultrasonic energy emitted from the rotating transducers 18 is generally in a conical beam as shown in FIG. 1 with a substantial radial component and a substantial axial component. The transducers 18 may have emitting and receiving sections 26 and 27 as shown in FIG. 2. or they may alternately be used as sensors and receivers. Electrical conductors 28 are provided which are electrically connected to the back sides of transducers 18 and are employed to transmit electricity to the transducers and to transmit electrical signals generated by the transducers upon receipt of reflected ultrasonic energy. The electrical signals are transmitted to the slip rings 29 and 30 on the proximal extremity of the rotatable shaft 16 and are electrically connected to conductors 31 and 32 which feed the signals to the display device or video monitor 33 shown in FIG. 7 which depicts a transverse outline of the wall defining the body lumen 11 at or closely adjacent to the cutting head 17 of the catheter 10.

As the catheter 10 is advanced through the occlusion 12, the physician can monitor the location of the cutting head 17 within the body lumen 11 to ensure that it is safely disposed within the center portion of the lumen. If the cutting head 17 diverges away from the center line of the body lumen 11 toward the wall forming the body lumen, the cutting head 17 rotation can be terminated or the position of the distal end of the catheter 10 can be reoriented so that no contact is made with the luminal wall. The orientation of the distal shaft section can be effected by one or more control lines 34 disposed within the wall of the catheter shaft 13. The four control lines 33 depicted in FIG. 3 allow for universal deflection of the distal portion of the catheter shaft 13 about the longitudinal axis of the catheter 10. Fluids may be introduced into the cutting field through the rotatable shaft lumen 23 from the arm 35 of adapter 15. Fluid and cutting debris may be aspirated from the cutting field through the passageways 22 in the supporting member 21 by applying a vacuum to lumen 14 through arm 36 of adapter 15.

The materials of construction of the catheter device of the invention may be conventional. For example, shaft 11 may be formed of polyethylene, polypropylene, polyvinyl chloride and thermoplastic polyurethane. The distal wall portion 25 may be an insert formed of material which transmits or is otherwise transparent to ultrasound. The rotatable shaft 16 may be made of high strength materials such as stainless steel, pseudoelastic NiTi alloys, cobalt-nickel-chromium alloys such as MR-35 sold by Carpenter Technology, Inc., PEEK (polyetheretherketone) polymer, polyamide and the like. The piezoelectric transducers 18 may be formed of conventional materials such as barium titanate or cinnabar. The cutting head 17 secured to the rotatable shaft 10 is also formed of a high strength material such as stainless steel and the like which can maintain a sharp cutting edge 36. The adapter 15 is preferably formed of a clear polycarbonate. A variety of other conventional materials may be used for making the components of the catheter device.

An alternative embodiment is shown in FIGS. 5 and 6. In this embodiment catheter 40 is an elongated shaft 41 with inner lumen 42. Cutting head 43 is mounted onto the distal end of rotatable shaft 44. A plurality of ultrasonic transducers 45 are mounted on shoulder 46 of the support member 47 which is secured to the distal end of shaft 48. Shaft 48 is fixed within the inner lumen 42 and does not move. The rotatable shaft 44 rotates within the inner lumen 50 of the fixed shaft 48. As in the prior embodiment, the support member 47 is provided with a plurality of passageways 51 to facilitate the aspiration of fluid and debris. At least one electrical conductor 52 is electrically connected to each of the transducers 45 which lead to slip rings (not shown) on the proximal end of the fixed shaft 48. In this embodiment the transducers 45 are sequentially activated rather than being rotated as in the first described embodiment. Similarly, the transducers are sequentially in a receiving mode to receive reflected ultrasonic energy and generate signals representative of the received ultrasonic energy. The signals generated are transmitted through conductors 52 and then processed to form an image of the outline of the body lumen as in the prior embodiment.

Figure 8:
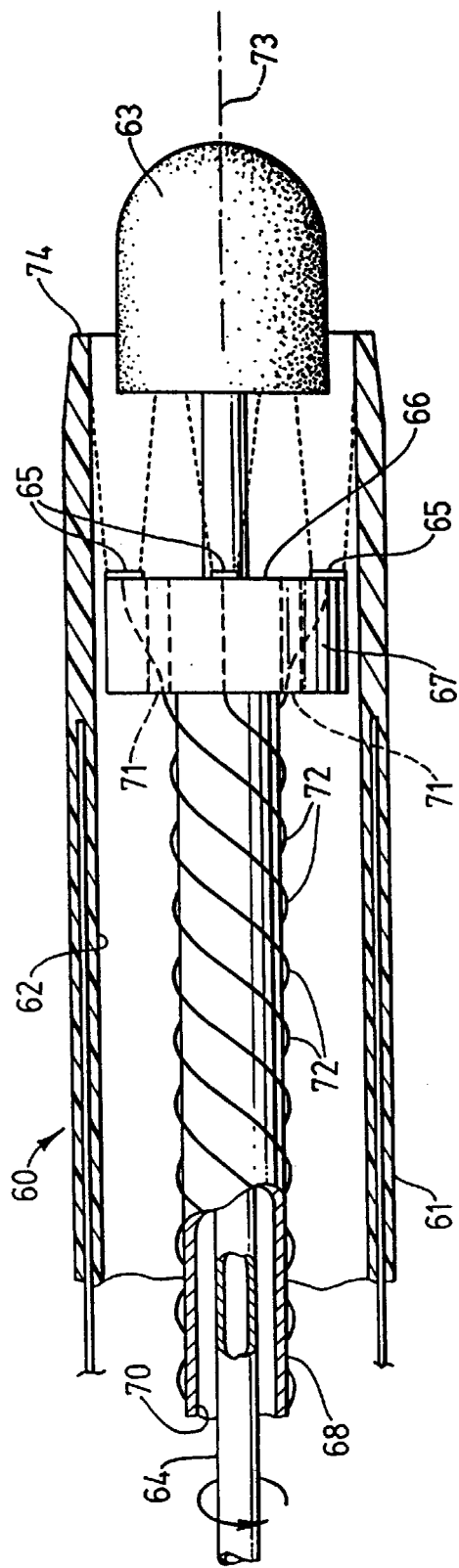
FIG. 8 is an elevational view, partially in section, of another alternative embodiment of the invention.

FIGS. 8 and 9 illustrate another embodiment of the invention which comprises a catheter 60 having an elongated shaft 61 with inner lumen 62. An abrasive head 63 is mounted onto the distal end of rotatable shaft 64 which is concentricly disposed within the shaft 61. A plurality of ultrasonic transducers 65 are mounted on distal face 66 of the support member 67 which is secured to the distal end of shaft 68. Shaft 68 is fixed within the inner lumen 62 and does not move. The rotatable shaft 64 rotates within the inner lumen 70 of the fixed shaft 68. As in the prior embodiment, the support member 67 is provided with a plurality of passageways 71 to facilitate the aspiration of fluids and debris therethrough. At least one conductor 72 is electrically connected to each of the ultrasonic transducer 65 which lead to slip rings (not shown) on the proximal end of the fixed shaft 68. In this embodiment the transducers 65 are sequentially activated rather than being rotated as in the first described embodiment. Similarly, the transducers are sequentially put in a receiving mode to receive reflected ultrasonic energy and generates signals representative of the received ultrasonic energy. The signals generated are transmitted through conductors 72 and then processed to form an image of the outline of the body lumen as in the prior embodiment. Rotation of the shaft 64 causes the rotation of the abrasive head 63 which in turn form a passageway through the occluding material. In this embodiment the ultrasonic energy for imaging is directed distally with the ultrasonic transducers generally being oriented perpendicular to the longitudinal axis 73 of the catheter 70. The distal tip 74 of the catheter shaft 61 is formed of suitable plastic material which transmits ultrasonic energy. The abrasive head may have finely divided abrasive particles on the surface thereof to provide the abrasive characteristics or a generally roughened surface may be provided for the same or similar effects.

In accordance with the present invention, there is not need to determine the nature or structure of the occluding material within the totally or near totally occluded body lumen. Of importance, is the outline of the wall defining the body lumen in which the occluding material is located so the physician can observe on a real time basis the location of the cutting head, abrasive head or other means used to remove occluding material to form a passageway within the body lumen to ensure that no contact is made with the wall forming the body lumen.

A variety of means may be used to remove occluding material in order to form the passageway through the occluded body lumen in addition to cutting and abrading means. For example, laser energy, ultrasonic energy, RF or microwave energy, auger type devices, high temperature probe tips, high pressure water jets and the like may be used to form the passageway. As used herein and the appended claims, reference to means to remove occluding material without further limitation, shall include any means to remove occluding material.

Although individual features of the various embodiments of the invention may be shown in some of the drawings and not in others, those skilled in the art will recognize that individual features of one embodiment of the invention can be combined with any or all the features of another embodiment. Additionally, various modifications and improvements can be made without departing from the scope of the invention.

What is claimed is:

1. A catheter system for recanalization of a totally or near totally occluded body lumen of a patient, comprising:
   a) a elongated catheter shaft having proximal and distal ends and an inner lumen extending therein;
   b) means at the distal end of the elongated catheter shaft to remove occluded body lumen;
   c) means disposed proximal to the distal end of the elongated catheter shaft and within the inner lumen extending therein to emit ultrasonic energy forward of the distal end of the catheter shaft toward a wall defining the body lumen;
   d) means to receive ultrasonic energy reflected from the wall defining the body lumen; and
   e) means to generate a transverse image of the wall from received reflected ultrasonic energy which indicates the radial position of the distal end of the elongated catheter shaft within the body lumen to aid an operator to maintain the means to remove occluding material at a desired radial position within the body lumen.

2. The system of claim 1 wherein the means to remove occluding material is mounted on a rotatable shaft.

3. The system of claim 2 wherein the means to remove occluding material has a cutting edge.

4. The system of claim 2 wherein the means to remove occluding material has an abrasive surface.

5. The system of claim 2 wherein the means to emit and receive ultrasonic energy are secured to the rotatable shaft.

6. The system of claim 5 wherein the means to emit and receive ultrasonic energy are secured to an inclined surface on a support member on the rotatable shaft.

7. The system of claim 6 wherein the support member is provided with at least one passageway therethrough to facilitate aspiration of fluid and debris.

8. The system of claim 6 wherein the elongated shaft has a wall portion is formed of material which readily transmits ultrasonic energy.

9. The system of claim 2 wherein a fixed shaft is disposed within the inner lumen of the elongated shaft and the means to emit and receive ultrasonic energy are secured to said fixed shaft.

10. The system of claim 9 wherein the fixed shaft is concentrically disposed about the rotatable shaft.

11. The system of claim 1 wherein the image display means is a video display unit.

12. The system of claim 1 wherein the means to emit ultrasonic energy is configured to emit ultrasonic energy in a direction having a substantial radial component.

13. The system of claim 1 wherein the means to emit ultrasonic energy is configured to emit ultrasonic energy in a direction having a substantial distal component.

14. The system of claim 1 wherein the means to emit ultrasonic energy is a piezoelectric crystal.

15. The system of claim 1 including means to direct the means for removing occluding material in a desired direction.

16. The system of claim 1 wherein the catheter has an inner lumen configured to slidably receive a guidewire to facilitate advancement of the catheter over the guidewire within the body lumen.

17. The system of claim 1 wherein the catheter shaft is sufficiently strong to transmit torque applied to the proximal end of the catheter to the distal end of the catheter.

18. A method for reanalyzing a totally or near totally occluded region of a body lumen within a patient which is defined at least in part by a cylindrical wall, comprising:

a) providing an elongated catheter having proximal and distal ends and an inner lumen extending therein, means at the distal end of the catheter to remove occluding material, means disposed proximal to the distal end of the elongated catheter shaft and within the inner lumen extending therein to emit ultrasonic energy and means to receive reflected ultrasonic energy, means to generate signals representing the received reflected ultrasonic energy and means to generate an transverse image of the body lumen based upon the signals representing the received reflected ultrasonic energy;

b) advancing the elongated catheter through the totally or near totally occluded body lumen while removing occluding material to form a channel therethrough by the means to remove occluding material;

c) emitting ultrasonic energy from the ultrasonic energy emitting means toward the wall distal to the distal end of the catheter;

d) receiving ultrasonic energy reflected from the wall;

e) generating signals representing the received ultrasonic energy reflected from the wall;

f) generating an image of the wall defining the body lumen based upon the signals representing the received reflected ultrasonic energy;

g) maintaining the location of the distal end of the catheter within the body lumen based upon the image generated of the wall; and h) removing occluding material to form a passageway through the occluded region of the body lumen.

19. The method of claim 18 wherein occluding material is removed by cutting with a rotating cutting head having a cutting edge.

20. The method of claim 18 wherein occluding material is removed by abrading with an rotating head with an abrasive surface.

21. The method of claim 18 wherein the catheter is advanced distally within the body lumen while removing occluding material.

* * * * *